(12) United States Patent
Hamilton et al.

(10) Patent No.: US 9,056,201 B1
(45) Date of Patent: *Jun. 16, 2015

(54) METHODS AND DEVICES FOR MINIMALLY-INVASIVE DELIVERY OF RADIATION TO THE EYE

(71) Applicant: SALUTARIS MEDICAL DEVICES, INC., Tucson, AZ (US)

(72) Inventors: Russell J. Hamilton, Tucson, AZ (US); Laurence J. Marsteller, Tucson, AZ (US); Michael Voevodsky, Grand Rapids, MI (US); Samuel Hyman, Tucson, AZ (US); Timothy Shriver, Vail, AZ (US)

(73) Assignee: SALUTARIS MEDICAL DEVICES, INC., Tucson, AZ (US)

( * ) Notice: Subject to any disclaimer, the term of this patent is extended or adjusted under 35 U.S.C. 154(b) by 70 days.

This patent is subject to a terminal disclaimer.

(21) Appl. No.: 14/011,516

(22) Filed: Aug. 27, 2013

Related U.S. Application Data

(60) Continuation-in-part of application No. 13/872,941, filed on Apr. 29, 2013, which is a division of application No. 12/350,079, filed on Jan. 7, 2009, now Pat. No. 8,430,804, application No. 14/011,516, which (Continued)

(51) Int. Cl.
*A61N 5/01* (2006.01)
*A61N 5/10* (2006.01)
(52) U.S. Cl.
CPC .............. *A61N 5/1017* (2013.01); *A61N 5/1007* (2013.01); *A61N 5/1048* (2013.01); *A61N 2005/1009* (2013.01)

(58) Field of Classification Search
CPC .............. A61N 5/10–5/1084; A61N 2005/1003–2005/1098
USPC .......... 600/1–8; 250/493.1–504 H; 252/625–647; 378/119–144; 424/1.11–1.89; 604/19–21
See application file for complete search history.

(56) References Cited

U.S. PATENT DOCUMENTS 2,309,302 A  1/1943 Butler et al.
2,559,793 A  7/1951 Pregel (Continued)

FOREIGN PATENT DOCUMENTS

AU  323700 S  1/2009
AU  323701 S  1/2009

(Continued)

OTHER PUBLICATIONS

Raghava et al.; Periocular routes for retinal drug delivery, 2004, pp. 99-114, Ashley Publications.

(Continued)

*Primary Examiner* — Catherine B Kuhlman
(74) *Attorney, Agent, or Firm* — Nguyen & Tarbet, LLC (57) ABSTRACT

Methods and devices for minimally-invasive delivery of radiation to the eye (such as the posterior portion of the eye) including cannulas with afterloading systems for introducing radionuclide brachytherapy sources to the cannulas, for example following insertion and positioning of the cannulas. The afterloaders may house the radionuclide brachytherapy source in a vault and connect to the cannula via a guide tube. The afterloaders can advance and retract the source and ensure accurate placement of the source within the cannula.

20 Claims, 5 Drawing Sheets

Related U.S. Application Data is a continuation-in-part of application No. 13/742,823, filed on Jan. 16, 2013, now Pat. No. 8,597,169, which is a continuation of application No. 12/497,644, filed on Jul. 3, 2009, now abandoned, which is a continuation-in-part of application No. 12/350,079, filed on Jan. 7, 2009, now Pat. No. 8,430,804, application No. 14/011,516, which is a continuation-in-part of application No. 13/111,780, filed on May 19, 2011, now Pat. No. 8,608,632, and a continuation-in-part of application No. 12/497,644, filed on Jul. 3, 2009, now abandoned, which is a continuation-in-part of application No. 12/350,079, filed on Jan. 7, 2009, now Pat. No. 8,430,804, application No. 14/011,516, which is a continuation-in-part of application No. 12/917,044, filed on Nov. 1, 2010, now abandoned, application No. 14/011,516, which is a continuation-in-part of application No. 13/111,765, filed on May 19, 2011, now Pat. No. 8,602,959, application No. 14/011,516, which is a continuation-in-part of application No. 13/953,528, filed on Jul. 29, 2013.

(60) Provisional application No. 61/347,226, filed on May 21, 2010, provisional application No. 61/010,322, filed on Jan. 7, 2008, provisional application No. 61/033,238, filed on Mar. 3, 2008, provisional application No. 61/035,371, filed on Mar. 10, 2008, provisional application No. 61/047,693, filed on Apr. 24, 2008, provisional application No. 61/376,115, filed on Aug. 23, 2010, provisional application No. 61/257,232, filed on Nov. 2, 2009, provisional application No. 61/347,233, filed on May 21, 2010, provisional appli­cation No. 61/676,783, filed on Jul. 27, 2012.

(56) References Cited

U.S. PATENT DOCUMENTS

| | | | |
|---|---|---|---|
| D183,820 S | 10/1958 | Yohe | |
| 3,169,527 A | 2/1965 | Sheridan | |
| 3,662,882 A | 5/1972 | Obermayer | |
| D235,171 S | 5/1975 | Boone | |
| D235,172 S | 5/1975 | Boone | |
| D236,920 S | 9/1975 | Sheridan | |
| 4,248,354 A | 2/1981 | Metzger | |
| 4,300,557 A | 11/1981 | Refojo et al. | |
| D272,089 S | 1/1984 | Glassman | |
| 4,925,450 A | 5/1990 | Imonti et al. | |
| 4,976,266 A | 12/1990 | Huffman et al. | |
| 5,007,689 A | 4/1991 | Kelly et al. | |
| 5,109,844 A | 5/1992 | de Juan, Jr. et al. | |
| 5,127,831 A | 7/1992 | Bab | |
| 5,167,647 A | 12/1992 | Wijkamp et al. | |
| 5,199,939 A | 4/1993 | Dake et al. | |
| D340,111 S | 10/1993 | Yoshikawa | |
| D345,417 S | 3/1994 | Sharipov | |
| D347,473 S | 5/1994 | Nitzsche | |
| 5,364,374 A | 11/1994 | Morrison et al. | |
| 5,392,914 A | 2/1995 | Lemieux et al. | |
| 5,399,298 A | 3/1995 | Kelly et al. | |
| 5,407,441 A * | 4/1995 | Greenbaum | 604/523 |
| 5,637,073 A | 6/1997 | Freire | |
| D390,656 S | 2/1998 | Linder | |
| 5,871,481 A | 2/1999 | Kannenberg et al. | |
| 5,893,873 A | 4/1999 | Rader et al. | |
| 5,935,155 A | 8/1999 | Humayun et al. | |
| 5,944,747 A | 9/1999 | Greenberg et al. | |
| 5,947,891 A | 9/1999 | Morrison | |
| 5,970,457 A | 10/1999 | Brant et al. | |
| 6,053,900 A | 4/2000 | Brown et al. | |
| D428,140 S | 7/2000 | Swan | |
| 6,135,984 A | 10/2000 | Dishler | |
| 6,149,643 A | 11/2000 | Herekar et al. | |
| 6,159,205 A | 12/2000 | Herekar et al. | |
| 6,183,410 B1 | 2/2001 | Jacobsen et al. | |
| 6,183,435 B1 | 2/2001 | Bumbalough et al. | |
| 6,278,975 B1 | 8/2001 | Brant et al. | |
| 6,302,839 B1 | 10/2001 | Chernomorsky et al. | |
| 6,402,734 B1 | 6/2002 | Weiss | |
| 6,413,245 B1 * | 7/2002 | Yaacobi et al. | 604/264 |
| 6,443,881 B1 | 9/2002 | Finger | |
| 6,450,938 B1 | 9/2002 | Miller | |
| 6,527,692 B1 | 3/2003 | Weinberger | |
| 6,575,887 B1 | 6/2003 | Schrayer | |
| 6,613,026 B1 | 9/2003 | Palasis et al. | |
| 6,641,518 B2 | 11/2003 | Wolfson et al. | |
| 6,676,590 B1 | 1/2004 | Urick et al. | |
| 6,719,750 B2 | 4/2004 | Varner et al. | |
| 6,749,553 B2 | 6/2004 | Brauckman et al. | |
| 6,755,338 B2 | 6/2004 | Hahnen et al. | |
| D492,778 S | 7/2004 | Narini | |
| 6,800,076 B2 | 10/2004 | Humayun | |
| 6,824,532 B2 | 11/2004 | Gillis et al. | |
| 6,830,174 B2 | 12/2004 | Hillstead et al. | |
| 6,875,165 B2 | 4/2005 | Dejuan, Jr. et al. | |
| 6,918,894 B2 | 7/2005 | Fleury et al. | |
| 6,958,055 B2 | 10/2005 | Donnan et al. | |
| 6,964,653 B2 | 11/2005 | Negron | |
| 6,977,264 B2 | 12/2005 | Fotsch et al. | |
| 7,070,556 B2 | 7/2006 | Anderson et al. | |
| 7,103,416 B2 | 9/2006 | Ok et al. | |
| 7,115,607 B2 | 10/2006 | Fotsch et al. | |
| 7,153,316 B1 | 12/2006 | McDonald | |
| D534,650 S | 1/2007 | Inman et al. | |
| D543,626 S | 5/2007 | Watschke et al. | |
| 7,217,263 B2 | 5/2007 | Humayun et al. | |
| 7,220,225 B2 | 5/2007 | Dejuan, Jr. et al. | |
| 7,223,225 B2 | 5/2007 | DeJuan, Jr. et al. | |
| 7,228,181 B2 | 6/2007 | Greenberg et al. | |
| 7,252,006 B2 | 8/2007 | Tai et al. | |
| 7,273,445 B2 | 9/2007 | Pulido et al. | |
| D553,738 S | 10/2007 | Simonson | |
| 7,276,019 B2 | 10/2007 | DeJuan, Jr. et al. | |
| 7,308,487 B1 | 12/2007 | Dansie et al. | |
| 7,321,796 B2 | 1/2008 | Fink et al. | |
| 7,351,193 B2 | 4/2008 | Forman et al. | |
| 7,357,770 B1 | 4/2008 | Cutrer et al. | |
| 7,402,155 B2 | 7/2008 | Palasis et al. | |
| D575,396 S | 8/2008 | Wu | |
| 7,485,113 B2 | 2/2009 | Varner et al. | |
| 7,503,474 B2 | 3/2009 | Hillstead et al. | |
| 7,537,593 B2 | 5/2009 | Humayun | |
| 7,547,323 B2 | 6/2009 | Lavigne | |
| 7,560,460 B2 | 7/2009 | Fotsch et al. | |
| 7,563,222 B2 | 7/2009 | Larsen et al. | |
| 7,571,004 B2 | 8/2009 | Roy et al. | |
| 7,579,347 B2 | 8/2009 | Bo et al. | |
| 7,600,533 B2 | 10/2009 | Tai et al. | |
| 7,654,716 B1 | 2/2010 | Bhadri et al. | |
| 7,661,676 B2 | 2/2010 | Smith et al. | |
| 7,684,868 B2 | 3/2010 | Tai et al. | |
| D615,645 S | 5/2010 | Brigatti et al. | |
| D616,087 S | 5/2010 | Brigatti et al. | |
| D616,088 S | 5/2010 | Brigatti et al. | |
| D616,540 S | 5/2010 | Brigatti et al. | |
| 7,729,739 B2 | 6/2010 | Acar et al. | |
| 7,744,520 B2 | 6/2010 | Larsen et al. | |
| 7,774,931 B2 | 8/2010 | Tai et al. | |
| 7,794,437 B2 | 9/2010 | Humayun et al. | |
| 7,803,102 B2 | 9/2010 | Larsen et al. | |
| 7,803,103 B2 | 9/2010 | Hillstead et al. | |
| 7,810,233 B2 | 10/2010 | Krulevitch et al. | |
| 7,827,038 B2 | 11/2010 | Richard et al. | |
| 7,831,309 B1 | 11/2010 | Humayun et al. | |
| 7,842,686 B2 | 11/2010 | Anderson et al. | |
| 7,846,954 B2 | 12/2010 | Zimmermann et al. | |
| 7,879,564 B2 | 2/2011 | Brice et al. | |
| 7,883,717 B2 | 2/2011 | Varner et al. | |
| 7,887,508 B2 | 2/2011 | Meng et al. | |
| D642,266 S | 7/2011 | Marsteller et al. | |
| 2001/0008950 A1 | 7/2001 | Vitali et al. | |

(56) References Cited

U.S. PATENT DOCUMENTS

| | | |
|---|---|---|
| 2001/0049464 A1 | 12/2001 | Ganz |
| 2002/0002362 A1 | 1/2002 | Humayun et al. |
| 2002/0026174 A1 | 2/2002 | Wallace |
| 2002/0062136 A1 | 5/2002 | Hillstead et al. |
| 2002/0065448 A1 | 5/2002 | Bradshaw et al. |
| 2002/0077687 A1 | 6/2002 | Ahn |
| 2002/0099363 A1 | 7/2002 | Woodward et al. |
| 2002/0115902 A1 | 8/2002 | Dejuan, Jr. et al. |
| 2002/0164061 A1 | 11/2002 | Paik et al. |
| 2002/0198511 A1 | 12/2002 | Varner et al. |
| 2003/0014306 A1 | 1/2003 | Marko |
| 2003/0045900 A1 | 3/2003 | Hahnen et al. |
| 2003/0103945 A1 | 6/2003 | Chen et al. |
| 2003/0153804 A1 | 8/2003 | Tornes et al. |
| 2003/0171722 A1 | 9/2003 | Paques et al. |
| 2003/0184859 A1 | 10/2003 | Liang et al. |
| 2003/0195201 A1 | 10/2003 | Bo et al. |
| 2003/0220324 A1 | 11/2003 | Fotsch et al. |
| 2004/0006067 A1 | 1/2004 | Fotsch et al. |
| 2004/0039312 A1 | 2/2004 | Hillstead et al. |
| 2004/0053309 A1 | 3/2004 | Holt et al. |
| 2004/0133155 A1 | 7/2004 | Varner et al. |
| 2004/0138515 A1 | 7/2004 | White et al. |
| 2004/0224777 A1 | 11/2004 | Smith et al. |
| 2004/0243176 A1 | 12/2004 | Hahnen et al. |
| 2005/0059956 A1 | 3/2005 | Varner et al. |
| 2005/0085415 A1* | 4/2005 | Wiesner et al. ............... 514/9 |
| 2005/0101824 A1 | 5/2005 | Stubbs |
| 2005/0107824 A1 | 5/2005 | Hillstead et al. |
| 2005/0148948 A1 | 7/2005 | Caputa |
| 2005/0149286 A1 | 7/2005 | Acar et al. |
| 2005/0177019 A1 | 8/2005 | DeJuan, Jr. et al. |
| 2005/0203331 A1 | 9/2005 | Szapucki et al. |
| 2005/0227986 A1 | 10/2005 | Bo et al. |
| 2005/0272931 A1 | 12/2005 | Bo et al. |
| 2005/0277802 A1 | 12/2005 | Larsen et al. |
| 2006/0009493 A1 | 1/2006 | Koenig et al. |
| 2006/0030618 A1 | 2/2006 | Bo et al. |
| 2006/0047255 A1* | 3/2006 | Kiehlbauch et al. .......... 604/294 |
| 2006/0052796 A1 | 3/2006 | Perez et al. |
| 2006/0078087 A1* | 4/2006 | Forman et al. ................. 378/65 |
| 2006/0110428 A1 | 5/2006 | deJuan et al. |
| 2006/0111605 A1 | 5/2006 | Larsen et al. |
| 2006/0142629 A1 | 6/2006 | DeJuan, Jr. et al. |
| 2006/0189838 A1 | 8/2006 | Dejuan, Jr. et al. |
| 2006/0223026 A1 | 10/2006 | Kuroiwa et al. |
| 2006/0235877 A1 | 10/2006 | Richard et al. |
| 2006/0257451 A1 | 11/2006 | Varner et al. |
| 2006/0287662 A1 | 12/2006 | Berry et al. |
| 2007/0019790 A1 | 1/2007 | Lewis et al. |
| 2007/0055089 A1 | 3/2007 | Larsen et al. |
| 2007/0118010 A1 | 5/2007 | Hillstead et al. |
| 2007/0179471 A1 | 8/2007 | Christian et al. |
| 2007/0219546 A1 | 9/2007 | Mody et al. |
| 2007/0233037 A1 | 10/2007 | Gifford, III et al. |
| 2007/0248545 A1 | 10/2007 | Brice et al. |
| 2007/0265248 A1 | 11/2007 | Fotsch et al. |
| 2007/0265485 A1 | 11/2007 | DeJuan, Jr. et al. |
| 2008/0027266 A1 | 1/2008 | Lebovic et al. |
| 2008/0108933 A1 | 5/2008 | Yu et al. |
| 2008/0154204 A1 | 6/2008 | Varner et al. |
| 2008/0161762 A1 | 7/2008 | Stehr et al. |
| 2008/0172086 A1 | 7/2008 | Hillstead et al. |
| 2008/0200467 A1 | 8/2008 | Wagner et al. |
| 2008/0214887 A1 | 9/2008 | Heanue et al. |
| 2008/0221653 A1 | 9/2008 | Agrawal et al. |
| 2008/0249412 A1 | 10/2008 | Huang et al. |
| 2008/0262512 A1 | 10/2008 | Humayun et al. |
| 2008/0262569 A1 | 10/2008 | Greenberg et al. |
| 2008/0262570 A1 | 10/2008 | Greenberg et al. |
| 2008/0262571 A1 | 10/2008 | Greenberg et al. |
| 2008/0272023 A1 | 11/2008 | McCormick et al. |
| 2008/0281142 A1 | 11/2008 | Lubock et al. |
| 2008/0281254 A1 | 11/2008 | Humayun et al. |
| 2008/0288036 A1 | 11/2008 | Greenberg et al. |
| 2008/0294223 A1 | 11/2008 | Greenberg et al. |
| 2008/0305320 A1 | 12/2008 | Laude et al. |
| 2008/0306611 A1 | 12/2008 | Rowley et al. |
| 2008/0319319 A1 | 12/2008 | Humayun et al. |
| 2009/0016075 A1 | 1/2009 | Bhadri et al. |
| 2009/0030323 A1 | 1/2009 | Fawzi et al. |
| 2009/0036827 A1 | 2/2009 | Cazzini |
| 2009/0069340 A1 | 3/2009 | Balestra et al. |
| 2009/0088784 A1 | 4/2009 | DeBoer et al. |
| 2009/0088843 A1 | 4/2009 | Lu et al. |
| 2009/0101841 A1 | 4/2009 | Boyden et al. |
| 2009/0104960 A1 | 4/2009 | Kelly et al. |
| 2009/0104987 A1 | 4/2009 | Kelly et al. |
| 2009/0112287 A1 | 4/2009 | Greenberg et al. |
| 2009/0131175 A1 | 5/2009 | Kelly et al. |
| 2009/0143124 A1 | 6/2009 | Hughes et al. |
| 2009/0143633 A1 | 6/2009 | Edmundson et al. |
| 2009/0143734 A1 | 6/2009 | Humayun et al. |
| 2009/0146583 A1 | 6/2009 | Bhadri et al. |
| 2009/0149915 A1 | 6/2009 | Greenberg et al. |
| 2009/0177245 A1 | 7/2009 | Ameri et al. |
| 2009/0192493 A1 | 7/2009 | Meng et al. |
| 2009/0227856 A1 | 9/2009 | Russell et al. |
| 2009/0228086 A1 | 9/2009 | Greenberg et al. |
| 2009/0240215 A1 | 9/2009 | Humayun et al. |
| 2009/0264424 A1 | 10/2009 | Bo et al. |
| 2009/0287276 A1 | 11/2009 | Greenberg et al. |
| 2009/0306585 A1 | 12/2009 | Pang et al. |
| 2009/0306594 A1 | 12/2009 | Pang et al. |
| 2009/0306595 A1 | 12/2009 | Shih et al. |
| 2009/0311133 A1 | 12/2009 | Pang et al. |
| 2009/0312742 A1 | 12/2009 | Pang et al. |
| 2010/0004499 A1 | 1/2010 | Brigatti et al. |
| 2010/0004581 A1 | 1/2010 | Brigatti et al. |
| 2010/0004639 A1 | 1/2010 | Pang et al. |
| 2010/0025613 A1 | 2/2010 | Tai et al. |
| 2010/0026957 A1 | 2/2010 | Tanguay, Jr. et al. |
| 2010/0030010 A1 | 2/2010 | Vermeere et al. |
| 2010/0076271 A1 | 3/2010 | Humayun |
| 2010/0100104 A1 | 4/2010 | Yu et al. |
| 2010/0105454 A1 | 4/2010 | Weber et al. |
| 2010/0114039 A1 | 5/2010 | Cazzini |
| 2010/0119696 A1 | 5/2010 | Yu et al. |
| 2010/0121248 A1 | 5/2010 | Yu et al. |
| 2010/0121249 A1 | 5/2010 | Yu et al. |
| 2010/0131075 A1 | 5/2010 | Ludlow et al. |
| 2010/0157620 A1 | 6/2010 | Bhadri et al. |
| 2010/0168646 A1 | 7/2010 | Greenbaum et al. |
| 2010/0174415 A1 | 7/2010 | Humayun et al. |
| 2010/0197826 A1 | 8/2010 | Agrawal et al. |
| 2010/0228119 A1 | 9/2010 | Brennan et al. |
| 2010/0228123 A1 | 9/2010 | Brennan et al. |
| 2010/0228124 A1 | 9/2010 | Brennan et al. |
| 2010/0228132 A1 | 9/2010 | Brennan et al. |
| 2010/0228238 A1 | 9/2010 | Brennan et al. |
| 2010/0229384 A1 | 9/2010 | Krulevitch et al. |
| 2010/0238288 A1 | 9/2010 | Klaerner et al. |
| 2010/0267647 A1 | 10/2010 | Greenbaum et al. |
| 2010/0268013 A1 | 10/2010 | Larsen et al. |
| 2010/0294041 A1 | 11/2010 | Tai et al. |
| 2010/0305550 A1 | 12/2010 | Meng et al. |
| 2011/0004045 A1 | 1/2011 | Larsen et al. |
| 2011/0021906 A1 | 1/2011 | Hillstead et al. |

FOREIGN PATENT DOCUMENTS

| | | |
|---|---|---|
| AU | 323703 S | 1/2009 |
| AU | 323704 S | 1/2009 |
| WO | 2005016258 A2 | 2/2005 |
| WO | 2007059208 A2 | 5/2007 |

OTHER PUBLICATIONS

Venkatesh et al.; Comparison of the Efficacy and Safety of Different Methods of Posterior Subtenon Injection; Ocular Immunology and Inflammation; Oct. 1, 2007; pp. 217-223; Infoma Healthcare USA, Inc.

Tenon's Capsule; Fundamentals and Principles; p. 39.

(56) References Cited

OTHER PUBLICATIONS

Canavan et al.; Sub-Tenon's administration of local anaesthetic: a review of the technique; 2003; pp. 787-793; British Journal of Anaesthesia.
Dafflon et al.; Posterior sub-Tenon's steriod injections for the treatment of posterior ocular inflammation: indications, efficacy and side effects, Graefe's Arch Clin Exp Ophthalmos, 1999, pp. 289-295; Springer-Verlag 1999.
Tanner et al.; Posterior sub-Tenon's triamcinolone injections in the treatment of uveitis; Royal College of Ophthalmologists; 1998; pp. 679-685.
Thach, MD et al.; A Comparison of Retrobulbar versus Sub-Tenon's Corticosteroid Therapy for Cystoid Macular Edema Refractory to Topical Medications; pp. 2003-2008; Ophthalmology Volue 104, No. 12, Dec. 1997.
Hubbard et al.; A New Ocular Brachytherapy System for the Treatment of Exudative AMD; 2005; Invest Ophthalmo Vis Sci 2005; 46; E-Abstract 2425.
Hubbard, III et al.; A Progress Report on the TheraSight Ocular Brachytherapy Safety and Feasibility Study; 2006; Invest Ophthalmol Vis Sci 2006; 47: E-Abstract 2101.
The Collaborative Ocular Melanoma Study Group; Design and Methods of a Clinical Trial for a Rare Condition: The Collaborative Ocular Melanoma Study; COMS Report No. 3; 1993; Controlled Clinical Trials 14: 362-391; Elsevier Science Publishing Co., Inc.
COMS Coordinating Center; Collaborative Ocular Melanoma Study; Manual of Procedures; Jan. 1995; pp. 1-330; The Wilmer Ophthalmological Institute; The Johns Hopkins School of Medicine (*reduced to cover and Table of Contents due to excessive data [330 pages]).
Hubbard et al.; Cadaver Evaluation of a New Ocular Brachytherapy System; Invest Ophthalmol Vis Sci 2004; 45: E-Abstract 5139.
Golden; SubTenon Injection of Gentamicin for Bacterial Infections of the Eye; pp. S271-S277; The Journal of Infectious Diseases; vol. 124, Supplement; Dec. 1971; University of Chicago.
Snyder, MD, PhD et al.; Antibiotic Therapy for Ocular Infection; Conferences and Reviews; pp. 579-584; WJM, Dec. 1994; vol. 161, No. 6; Therapy for Ocular Infection—Snyder and Glasser.
Baum, M.D. et al.; The Evolution of Antibiotic Therapy for Facterial Conjunctivitis and Keratitis: 1970-2000; pp. 659-672; Cornea, vol. 19, No. 5, 2000; Lippincott Williams & Wilkins, Inc., Philadelphia.
Scoper; Review of Third- and Fourth-Generation Fluoroquinolones in Ophthalmology: In-Vitro and In-Vivo Efficacy; Adv Ther. 2008; 25(10): 979-994; Springer Healthcare Communications.
Yilmaz, MD et al.; Severe Fungal Keratitis Treated With Subconjunctival Fluconazole; 2003; pp. 454.e1-454.e7; vol. 140, No. 3; Elsevier Inc.
Yilmaz, MD et al.; Severe Fungal Keratitis Treated With Subconjunctival Fluconazole; Apr. 2006; pp. 783-784; vol. 141, No. 4, Correspondence; American Journal of Ophthalmology.
Ikewaki et al.; Peribulbar fungal abscess and endophthalmitis following posterior subtenon injection of triamcinolone acetonide; Diagnolis/Therapy in Ophthalmology; 2008; pp. 102-104; Acta Ophthalmologica; The Authors, Journal compilation, Acta Ophthalmol.
Nayak et al.; Acute orbital abscess complicating deep posterior subtenon triamcinolone injection; Indian Journal of Ophthalmology; vol. 56, No. 3; May-Jun. 2008; downloaded from http://www.ijo.in on Monday, Nov. 2, 2009.
Kusaka et al.; Orbital infection following posterior subtenon triamcinolone injection; 2207; pp. 692-693; Acta Ophthalmologica Scandinavica.
Walker et al.; Conservative management of refractory steroid-induced glaucoma following anterior subtenon steroid injection; 2007; Letters to the Editor; pp. 197-198; The Authors, Journal compilation, Royal Australian and New Zealand College of Ophthalmologists.
Au et al.; Localised abscess following an injection of subtenon triamcinolone acitonide; Correspondence; Eye (2007) 21, 627-674, doi:10.1038/sj.eye.6702671; published online Dec. 15, 2006.
Venkatesh MD, et al.; Posterior subtenon injection of corticosteroids using polytetrafluoroethylene (PEFE) intravenous cannula; Clinical and Experimental Ophthalmology (2002) 30, 55-57; All India Institute of Medical Sciences Campus, India.
Sou-Tung Chiu-Tsao, Ph.D., Episcleral Eye Plaques for Treatment of Intraocular Malignancies and Benign Diseases; Chapter 34; pp. 673-705.
Sou-Tung Chiu-Tsao, Ph.D., Pterygium Brachytherapy Physics; Chapter 35; pp. 707-717.
Nath, Ravinder, Ph.D. et al.; Brachytherapy Physics Second Edition; Medical Physics Monograph No. 31; 1013 pages; Medical Physics Publishing; Madison, Wisconsin, USA; 2005.
Jaakkola, Aino; Heikkonen, Jorma; Tarkkanen, Ahti and Immonen, Ilkka; Visual function after strontium-90 plaque irradiation in patients with age-related subfoveal choroidal neovascularization; Acta Opthalmologica Scandinavica 1999; 77; pp. 57-61.
Hokkanen, J.; Heikkonen, J.; Holmberg, P.; Theoretical calculations of dose distributions for beta-ray eye applicators; Med. Phys. 24 (2); Feb. 1997pp. 211-213.
Jaakkola, Aino; Heikkonen, Jorma; Tommila, Petri; Laatikainen, Leila; Immonen, Ilkka; Strontium plaque irradiation of subfoveal neovascular membranes in age-related macular degeneration; Graefe's Arch Clin Exp Ophthalmol (1998); 236; pp. 24-30.
JC Wen et al; Ocular complications following I-125 brachytherapy for choroidal melanoma; Eye; 2009; 23; 1254-1268.
Messmer E et al.; Histopathologic findings in eyes treated with a ruthenium plaque for uveal melanoma; Graefes Arch Clin Exp Opthalmol.; 1992; 230 (4): 391-6.
J. M. Capping; Radiation scleral necrosis simulating early scleromalacia perforans; Brit. J. Ophthal.; 1973; 57; pp. 425-428.

* cited by examiner

METHODS AND DEVICES FOR MINIMALLY-INVASIVE DELIVERY OF RADIATION TO THE EYE

CROSS REFERENCE

This application claims priority to U.S. patent application Ser. No. 13/872,941, filed Apr. 29, 2013, which is a division of U.S. patent application Ser. No. 12/350,079, filed Jan. 7, 2009, which is a non-provisional of U.S. Provisional Application No. 61/010,322, filed Jan. 7, 2008, U.S. Provisional Application No. 61/033,238, filed Mar. 3, 2008, U.S. Provisional Application No. 61/035,371, filed Mar. 10, 2008, and U.S. Provisional Application No. 61/047,693, filed Apr. 24, 2008, the specification(s) of which is/are incorporated herein in their entirety by reference.

This application also claims priority to U.S. patent application Ser. No. 13/742,823, filed Jan. 16, 2013, which is a continuation of U.S. patent application Ser. No. 12/497,644, filed Jul. 3, 2009, which is a continuation-in-part of U.S. patent application Ser. No. 12/350,079, filed Jan. 7, 2009, which is a non-provisional of U.S. Provisional Application No. 61/010,322, filed Jan. 7, 2008, U.S. Provisional Application No. 61/033,238, filed Mar. 3, 2008, U.S. Provisional Application No, 61/035,371, filed Mar. 10, 2008, and U.S. Provisional Application No. 61/047,693, filed Apr. 24, 2008, the specification(s) of which is/are incorporated herein in their entirety by reference.

This application also claims priority to U.S. patent application Ser. No. 13/111,780, filed May 19, 2011, which is a non-provisional of U.S. Provisional Application No. 61/347,226, filed May 21, 2010; and a continuation-in-part of U.S. patent application Ser. No. 12/497,644, filed Jul. 3, 2009, which is a continuation-in-part of U.S. patent application Ser. No. 12/350,079, filed Jan. 7, 2009, which is a non-provisional of U.S. Provisional Application No. 61/010,322, filed Jan. 7, 2008, U.S. Provisional Application No. 61/033,238, filed Mar. 3, 2008, U.S. Provisional Application No. 61/035,371, filed Mar. 10, 2008, and U.S. Provisional Application No. 61/047,693, filed Apr. 24, 2008, the specification(s) of which is/are incorporated herein in their entirety by reference.

This application also claims priority to U.S. patent application Ser. No. 12/917,044, filed Nov. 1, 2010, which is a non-provisional of U.S. Provisional Application No. 61/257,232, filed Nov. 2, 2009 and U.S. Provisional Application No. 61/376,115, filed Aug. 23, 2010, the specification(s) of which is/are incorporated herein in their entirety by reference.

This application also claims priority to U.S. patent application Ser. No. 13/111,765, filed May 19, 2011, which is a non-provisional of U.S. Provisional Application No. 61/347,233, filed May 21, 2010, the specification(s) of which is/are incorporated herein in their entirety by reference.

This application also claims priority to U.S. patent application Ser. No. 13/953,528, filed Jul. 29, 2013, which is a non-provisional of U.S. Provisional Application No. 61/676,783, filed Jul. 27, 2012, the specification(s) of which is/are incorporated herein in their entirety by reference.

FIELD OF THE INVENTION

The present invention relates to methods and devices for introducing radiation to the eye, e.g., the posterior portion of the eye, for treating and/or managing eye conditions including but not limited to macular degeneration.

BACKGROUND OF THE INVENTION

The present invention features methods and devices for minimally-invasive delivery of radiation to the eye, e.g., the posterior portion of the eye. For example, the present invention features cannulas and afterloading systems (e.g., remote afterloading systems) for introducing radionuclide brachytherapy sources (RBS) to the cannulas for irradiating targets (e.g., targets of the eye). The RBS may be, for example, introduced into the cannula via an afterloading system following cannula insertion and positioning.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

The present invention features methods of irradiating a target of an eye in a patient. In some embodiments, the method comprises (a) inserting a cannula into a potential space between a sclera and a Tenon's capsule of the eye of the patient, wherein the cannula is operatively connected to an afterloading system having a radionuclide brachytherapy source (RBS); (b) positioning the RBS over the target; (c) irradiating the target with the RBS; and (d) removing the cannula.

In some embodiments, the method comprises (a) inserting a cannula into a potential space between a sclera and a Tenon's capsule of the eye of the patient, wherein the cannula is operatively connected to an afterloading system having a radionuclide brachytherapy source (RBS); (b) placing a distal portion of the cannula on or near the sclera and positioning a treatment position(s) of the cannula (e.g., of the distal portion of the cannula) near the target; (c) advancing the RBS from the afterloading system through the cannula (100) to the treatment position(s) in the distal portion of the cannula; (d) exposing the target to the RBS; (e) retracting the RBS; and (f) removing the cannula.

In some embodiments, the method comprises (a) inserting a cannula into a potential space between a sclera and a Tenon's capsule of the eye of the patient; (b) placing a distal portion of the cannula on or near the sclera and positioning a treatment position(s) of the distal portion of the cannula near the target; (c) operatively connecting an afterloading system having a radionuclide brachytherapy source (RBS) to the cannula; (d) advancing the RBS from the afterloading system through the cannula to the treatment position(s) in the distal portion of the cannula; (e) exposing the target to the RBS; and (f) retracting the RBS; and (g) removing the cannula.

In some embodiments, the afterloading system comprises (a) a vault for storage of the RBS, wherein the RBS is attached to an advancing means; (b) a guide tube extending from the vault, wherein the guide tube is removably attachable to the cannula; and (c) a source-drive mechanism operatively connected to the advancing means, wherein the source-drive mechanism advances the RBS through the guide tube to the treatment position(s) in the cannula. In some embodiments, the source-drive mechanism retracts the RBS from the treatment position(s).

In some embodiments, the source-drive mechanism comprises a motor. In some embodiments, the motor comprises drive rollers or belts. In some embodiments, the source-drive mechanism is operatively connected to a computer or other controller. In some embodiments, the computer or other controller is operatively connected to a control console, the control console allows for manipulation of the computer or other controller. In some embodiments, the afterloading system measures dwell time of the RBS in the treatment position(s).

In some embodiments, the afterloading system moves the RBS from the vault to the treatment position(s) at a rate of between about 0.01 m/s to about 4 m/s. In some embodiments, the afterloading system moves the RBS from the vault to the treatment position(s) at a rate of between about 2 m/s. In some embodiments, the RBS is a high-dose-rate (HDR) source. In some embodiments, the RBS provides a dose rate of between about 2 to 10 Gy/min to the target. In some embodiments, the RBS provides a dose rate of between about 1 to 10 Gy/min to the target. In some embodiments, the RBS provides a dose rate of between about 2 to 6 Gy/min to the target. In some embodiments, the RBS provides a dose rate of about 4.4 Gy/min to the target.

In some embodiments, the cannula comprises a distal portion and a proximal portion connected by an inflection point, the distal portion has a radius of curvature between about 9 to 15 mm and an arc length between about 25 to 35 mm and the proximal portion has a radius of curvature between about an inner cross-sectional radius of the cannula and about 1 meter. In some embodiments, the cannula is flexible. In some embodiments, the cannula has a fixed shape.

In some embodiments, the afterloader system is operatively connected to the cannula after the cannula is positioned in between the Tenon's capsule and sclera. In some embodiments, the afterloader system is operatively connected to the cannula before the cannula is positioned in between the Tenon's capsule and sclera. In some embodiments, both (a) the afterloader system is operatively connected to the cannula and (b) the RBS is advanced before the cannula is positioned in between the Tenon's capsule and sclera.

The present invention also features brachytherapy systems. In some embodiments, the brachytherapy system comprises (a) a cannula for insertion into a potential space between a sclera and a Tenon's capsule of an eye of a patient; and (b) an afterloading system operatively connected to the cannula. In some embodiments, the afterloading system comprises: a vault for storage of a radionuclide brachytherapy source (RBS), wherein the RBS is attached to an advancing means; a guide tube extending from the vault, wherein the guide tube is removably attachable to the cannula; and a source-drive mechanism operatively connected to the advancing means, wherein the source-drive mechanism advances the RBS through the guide tube to the treatment position(s) in the cannula. In some embodiments, the afterloader system is attached to the cannula via a connector.

DESCRIPTION OF PREFERRED EMBODIMENTS

Following is a list of elements corresponding to a particular element referred to herein:

100 cannula
110 distal portion of cannula
118 treatment position
120 proximal portion of cannula
130 inflection point of cannula
150 connector (optional)
400 radionuclide brachytherapy source (RBS)
700 afterloading system
710 vault
720 guide tube
722 advancing means (e.g., guide wire)
730 source-drive mechanism
732 motor
740 computer (e.g., microprocessor)
744 control console Referring now to FIG. 1-4, the present invention features methods and devices for minimally-invasive delivery of radiation to the eye, e.g., the posterior portion of the eye. For example, the present invention features afterloading systems (700) (e.g., remote afterloading systems) for introducing a radionuclide brachytherapy source (RBS) (400) to a cannula (100). The cannula (100) may be adapted for insertion into a potential space between the sclera and the Tenon's capsule of the eye of a patient.

The present methods and devices may be effective for treating and/or managing a condition (e.g., an eye condition). For example, the present methods and devices may be used to treat and/or manage wet (neovascular) age-related macular degeneration. The present methods are not limited to treating and/or managing wet (neovascular) age-related macular degeneration. For example, the present methods may also be used to treat and/or manage conditions including macular degeneration, abnormal cell proliferation, choroidal neovascularization, retinopathy (e.g., diabetic retinopathy, vitreoretinopathy), macular edema, and tumors (e.g., intra ocular melanoma, choroidal melanoma, retinoblastoma).

Cannula

Figure 1:
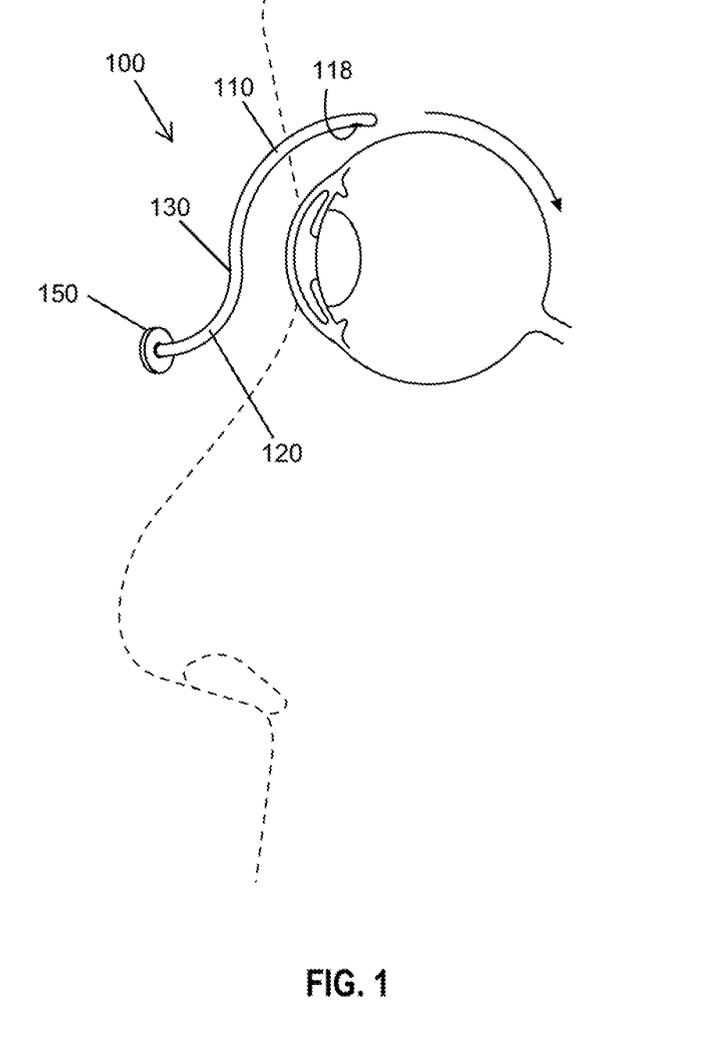
FIG. 1 shows an in-use view of a cannula of the present invention.

As shown in FIG. 1, the cannula (100) comprises a distal portion (110) and a proximal portion (120) connected by an inflection point (130). The distal portion (110) is generally for placement around a portion of the globe of the eye. In some embodiments, the distal portion (110) has a radius of curvature between about 9 to 15 mm and an arc length between about 25 to 35 mm. In some embodiments, the proximal portion (120) has a radius of curvature between about an inner cross-sectional radius of the cannula (100) and about 1 meter. The cannula (100), or a portion thereof, may be flexible, fixed-shape, or a combination thereof. The cannula (100) is not limited to the aforementioned dimensions and configurations.

Figure 2:
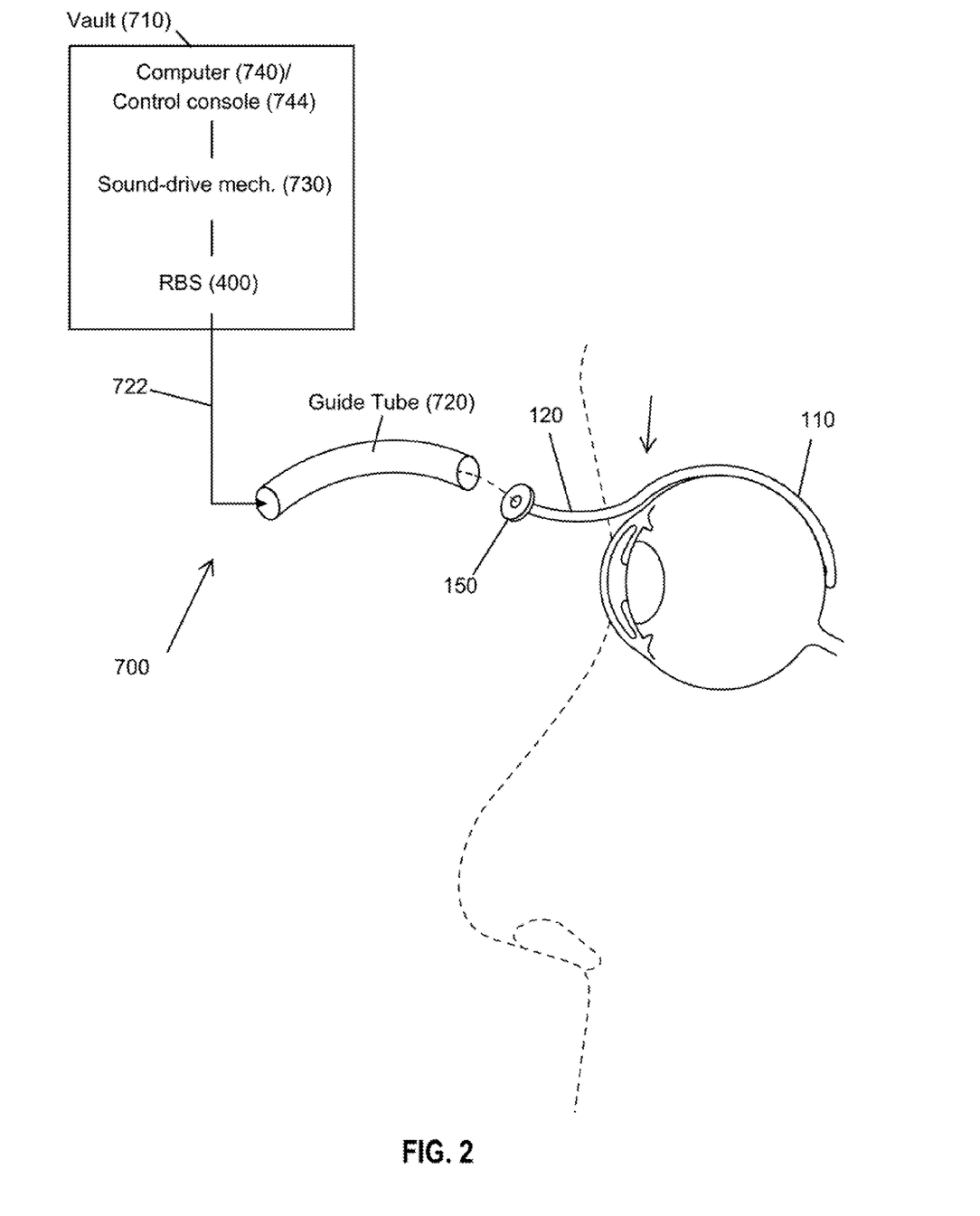
FIG. 2 shows a schematic view of an afterloading system attachable to a cannula.

The cannula (100) may be operatively connected to an afterloading system (700) having a radionuclide brachytherapy source (RBS) (400). The afterloading system (700) can deliver the RBS (400) to the cannula (100) (e.g., to a treatment position (118) of the cannula (100), to at least one treatment position, to one or more treatment positions, etc.). For example, the afterloading system (700) can direct the RBS (400) to a position within the cannula (100) (e.g., a treatment position (118), at least one treatment position, one or more treatment positions, etc.) such that the RBS (400) is over a target. The RBS (400) can then irradiate the target for a length of time desired. The afterloading system (700) may also function to remove the RBS (400) from the position within the cannula (e.g., the treatment position(s) (118)) and from the cannula (100) altogether. For example, the afterloading system (700) may retract the RBS (400) to its starting position outside of the cannula (100).

The cannula (100) may comprise one or more treatment positions (118). The afterloading system (700) may function to deliver one or more RBSs (400) to one or more treatment positions (118).

In some embodiments, the cannula (100) is inserted, e.g., into the potential space between the sclera and the Tenon's capsule, and is positioned appropriately prior to attachment of the afterloading system (700). For example, the distal portion (110) of the cannula is placed on or near the sclera and the treatment position(s) (118) of the cannula (100) (e.g., in the distal portion (110)) or treatment position(s), is positioned near the target. Following placement and positioning of the cannula, the afterloading system (700) may be connected to the cannula. In some embodiments, the cannula (100) and the afterloading system (700) are connected prior to insertion of the cannula (100), e.g., into the potential space between the sclera and the Tenon's capsule.

Afterloading System

Figure 3:
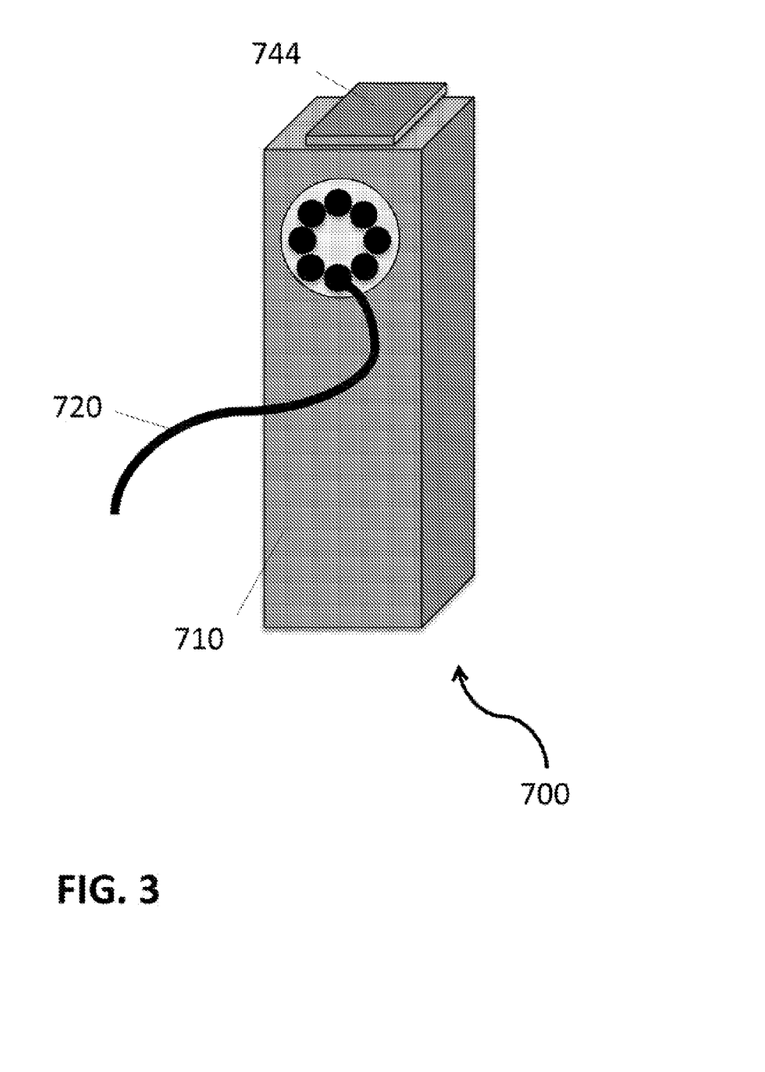
FIG. 3 shows a schematic view of an afterloading system of the present invention. Afterloading systems are well known to one of ordinary skill in the art. The present invention is not limited to the afterloading systems described herein.
Figure 4A:
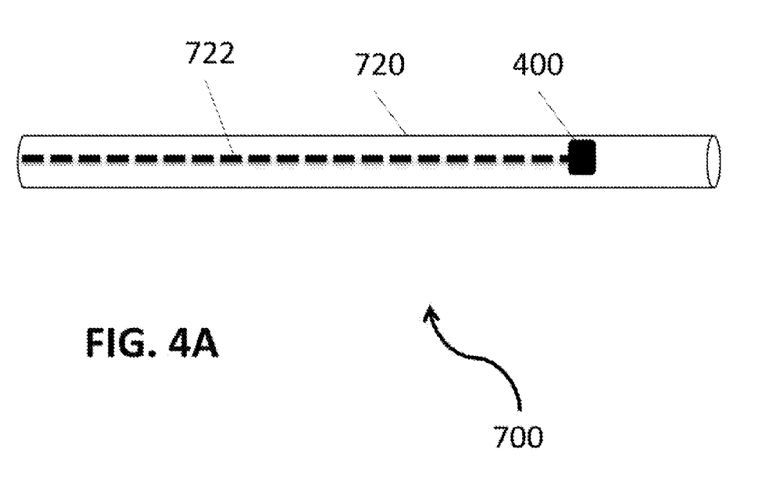
FIG. 4A shows the advancing means and RBS within the guide tube.
Figure 4B:
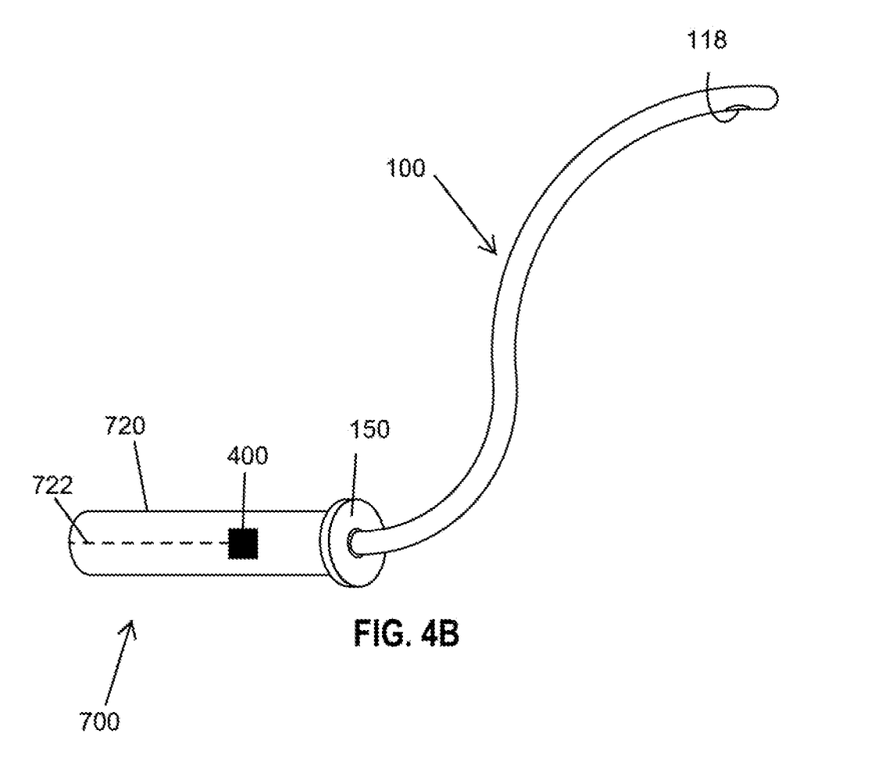
FIG. 4B shows the guide tube connecting to the cannula.

The afterloading system (700) may allow for accurate placement of the RBS (400), e.g., at the treatment position(s) (118) within the cannula (100). Afterloading systems (700) are well known to one of ordinary skill in the art and any appropriate afterloading system (700) may be utilized. For example, in some embodiments, the afterloading system (700) comprises a vault (710) for temporary housing of the RBS (400). The RBS (400) may be attached to an advancing means (722) (e.g., a guide wire). In some embodiments, the RBS (400) may be incorporated into the advancing mean (722) (e.g., guide wire). The advancing means (722) (e.g., guide wire) may be constructed from any appropriate material including but not limited to nitinol and stainless steel. A guide tube (720) extends from the vault (710) and is connected to the cannula (100). In some embodiments, the guide tube (720) connects, e.g., removably connects, to the cannula (100) via a connector (150). In some embodiments, the connector (150) is disposed on the cannula (100), e.g., on the proximal portion (120) of the cannula (100). The advancing means (722) directs the RBS (400) through the guide tube (720), e.g., the advancing means (722) may be disposed in at least a portion of the guide tube (720).

The afterloading system (700) comprises a source-drive mechanism (730) operatively connected to the advancing means (722) (e.g., guide wire). The source-drive mechanism (730) functions to advance the advancing means (722) (e.g., guide wire) and RBS (400) through the guide tube (720) to the treatment position(s) (118) in the cannula (100). In some embodiments, the source-drive mechanism (730) comprises a motor (732). In some embodiments, the motor (732) comprises drive rollers or belts.

In some embodiments, the afterloading system (700) comprises a computer (740) (e.g., a microprocessor) or other controller (e.g., an analog or a mechanical control system). The motor (7320) and/or source-drive mechanism (730) may be operatively connected to the computer (740) or other controller. In some embodiments, the computer (740) or other controller is operatively connected to a control console (744). The control console (744) allows for manipulation of the computer (740) or other controller. For example, the control console (744) may allow for programming of the afterloading system (700), e.g., dwell time of the RBS (400) in the treatment position(s) (118), speed of delivery of the RBS (400), etc. In some embodiments, the afterloading system (700) moves the RBS (400) from the vault (710) to the treatment position(s) (118) at a rate of between about 0.01 m/s (1 cm/s) to about 4 m/s. In some embodiments, the afterloading system (700) moves the RBS (400) from the vault (710) to the treatment position(s) (118) at a rate of about 2 m/s.

The afterloading system (700) may measure various parameters of the treatment. For example, in some embodiments, the afterloading system (700) measures dwell time of the RBS (400) in the treatment position(s) (118).

In some embodiments, the guide tube (720) is constructed from a material that provides some shielding from the radiation emitted from the RBS (400) as it travels through the guide tube (720)

In some embodiments, the afterloader system (700) further comprises a selector, for example for treatments that require multiple applicators or cannulas (100). The selector may provide multiple channels, e.g., between 1 to 10 channels, between 2 to 10 channels, between 2 to 20 channels, between 16 to 24 channels, between 18 to 24 channels, more than 24 channels, etc. The selector may facilitate the movement (e.g., entry, transfer) of the RBS (400) through multiple applicators (e.g., cannulas (100)), if necessary.

Radionuclide Brachytherapy Source

The methods and devices of the present invention may feature any appropriate RBS (400). In some embodiments, the RBS (400) is a high-dose-rate (HDR) source. In some embodiments, the RBS (400) is a low-dose-rate (LDR) source. In some embodiments, the RBS (400) is a pulsed-dose-rate (PDR) source. In some embodiments, the RBS (400), e.g., HDR source, delivers a dose rate greater than 100 cGy per minute for a length of time. However the present invention is not limited to a HDR source that delivers a dose rate greater than 100 cGy per minute. In some embodiments, the RBS (400) provides a dose rate of between about 2 to 10 Gy/min to the target. In some embodiments, the RBS (400) provides a dose rate of between about 1 to 10 Gy/min to the target. In some embodiments, the RBS (400) provides a dose rate of between about 2 to 6 Gy/min to the target. In some embodiments, the RBS (400) provides a dose rate of about 4.4 Gy/min to the target. In some embodiments, a LDR source provides a dose rate of less than about 2 Gy/hour. In some embodiments, a medium-dose-rate (MDR) source provides a dose rate of between about 2 to 12 Gy/hour. In some embodiments, a HDR source provides a dose rate of greater than about 12 Gy/hour.

In some embodiments, the RBS (400) provides a dose rate of greater than about 10 Gy/min. In some embodiments, the RBS (400) provides a dose rate of greater than about 11 Gy/min to the target. In some embodiments, the RBS (400) provides a dose rate of greater than about 12 Gy/min to the target. In some embodiments, the RBS (400) provides a dose rate of greater than about 13 Gy/min to the target. In some embodiments, the RBS (400) provides a dose rate of greater than about 14 Gy/min to the target. In some embodiments, the RBS (400) provides a dose rate of greater than about 15 Gy/min to the target. In some embodiments, the RBS (400) provides a dose rate between about 10 to 15 Gy/min. In some embodiments, the RBS (400) provides a dose rate between about 15 to 20 Gy/min. In some embodiments, the RBS (400) provides a dose rate between about 20 to 30 Gy/min. In some embodiments, the RBS (400) provides a dose rate between about 30 to 40 Gy/min. In some embodiments, the RBS (400) provides a dose rate between about 40 to 50 Gy/min. In some embodiments, the RBS (400) provides a dose rate between about 50 to 60 Gy/min. In some embodiments, the RBS (400) provides a dose rate between about 60 to 70 Gy/min. In some embodiments, the RBS (400) provides a dose rate between about 70 to 80 Gy/min. In some embodiments, the RBS (400) provides a dose rate between about 80 to 90 Gy/min. In some embodiments, the RBS (400) provides a dose rate between about 90 to 100 Gy/min. In some embodiments, the RBS (400) provides a dose rate of greater than 100 Gy/min.

In some embodiments, the RBS (400) provides a dose rate between about 15 to 20 Gy/min to the target. In some embodiments, the RBS (400) provides a dose rate between about 20 to 25 Gy/min to the target. In some embodiments, the RBS (400) provides a dose rate between about 25 to 30 Gy/min to the target. In some embodiments, the RBS (400) provides a dose rate between about 30 to 35 Gy/min to the target. In some embodiments, the RBS (400) provides a dose rate between about 35 to 40 Gy/min to the target. In some embodiments, the RBS (400) provides a dose rate between about 40 to 50 Gy/min to the target. In some embodiments, the RBS (400) provides a dose rate between about 50 to 60 Gy/min to the target. In some embodiments, the RBS provides a dose rate between about 60 to 70 Gy/min to the target. In some embodiments, the RBS (400) provides a dose rate between about 70 to 80 Gy/min to the target. In some embodiments, the RBS (400) provides a dose rate between about 80 to 90 Gy/min to the target. In some embodiments, the RBS (400) provides a dose rate between about 90 to 100 Gy/min to the target. In some embodiments, the RBS (400) provides a dose rate greater than about 100 Gy/min to the target, As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A method of irradiating a target of an eye in a patient, said method comprising:
    (a) inserting a cannula (100) into a potential space between a sclera and a Tenon's capsule of the eye of the patient, the cannula (100) is operatively connected to an afterloading system (700) having a radionuclide brachytherapy source (RBS) (400);
    (b) placing a distal portion (110) of the cannula (100) on or near the sclera and positioning a treatment position (118) of the distal portion (110) of the cannula (100) near the target;
    (c) advancing the RBS (400) from the afterloading system (700) through the cannula (100) to the treatment position (118) in the distal portion (110) of the cannula (110);
    (d) exposing the target to the RBS (400);
    (e) retracting the RBS (400); and
    (f) removing the cannula (100).

2. The method of claim 1, wherein the afterloading system (700) comprises:
    (a) a vault (710) for storage of the RBS (400), wherein the RBS (400) is attached to an advancing means (722);
    (b) a guide tube (720) extending from the vault (710), the guide tube (720) is removably attachable to the cannula (100); and
    (c) a source-drive mechanism (730) operatively connected to the advancing means (722), wherein the source-drive mechanism (730) advances the RBS (400) through the guide tube (720) to the treatment position (118) in the cannula (100) and retracts the RBS (400) from the treatment position (118).

3. The method of claim 2, wherein the source-drive mechanism (730) is operatively connected to a computer (740) or other control system.

4. The method of claim 3, wherein the computer (740) or other control system is operatively connected to a control console (744), the control console (744) allows for manipulation of the computer (740) or other control system.

5. The method of claim 1, wherein the afterloading system (700) measures dwell time of the RBS (400) in the treatment position (118).

6. The method of claim 1, wherein the RBS (400) provides a dose rate of between about 1 to 10 Gy/min to the target.

7. The method of claim 1, wherein the cannula (100) comprises a distal portion (110) and a proximal portion (120) connected by an inflection point (130), the distal portion (110) has a radius of curvature between about 9 to 15 mm and an arc length between about 25 to 35 mm and the proximal portion (120) has a radius of curvature between about an inner cross-sectional radius of the cannula (100) and about 1 meter.

8. The method of claim 1, wherein the afterloader system (700) is operatively connected to the cannula (100) after the cannula (100) is positioned in between the Tenon's capsule and sclera.

9. The method of claim 1, wherein the afterloader system (700) is operatively connected to the cannula (100) before the cannula is positioned in between the Tenon's capsule and sclera.

10. The method of claim 1, wherein both (a) the afterloader system (700) is operatively connected to the cannula (100) and (b) the RBS (400) is advanced before the cannula (100) is positioned in between the Tenon's capsule and sclera.

11. A method of irradiating a target of an eye in a patient, said method comprising:
    (a) inserting a cannula (100) into a potential space between a sclera and a Tenon's capsule of the eye of the patient;
    (b) placing a distal portion (110) of the cannula (100) on or near the sclera and positioning a treatment position (118) of the distal portion (110) of the cannula (100) near the target;
    (c) operatively connecting an afterloading system (700) having a radionuclide brachytherapy source (RBS) (400) to the cannula (100);
    (d) advancing the RBS (400) from the afterloading system (700) through the cannula (100) to the treatment position (118) in the distal portion (110) of the cannula (110);
    (e) exposing the target to the RBS (400); and
    (f) retracting the RBS (400); and
    (g) removing cannula (100).

12. The method of claim 11, wherein the afterloading system (700) comprises:

(a) a vault (710) for storage of the RBS (400), wherein the RBS (400) is attached to an advancing means (722);

(b) a guide tube (720) extending from the vault (710), the guide tube (720) is removably attachable to the cannula (100); and (c) a source-drive mechanism (730) operatively connected to the advancing means (722), wherein the source-drive mechanism (730) advances the RBS (400) through the guide tube (720) to the treatment position (118) in the cannula (100) and retracts the RBS (400) from the treatment position (118).

13. The method of claim 12, wherein the source-drive mechanism (730) is operatively connected to a computer (740) or other control system.

14. The method of claim 13, wherein the computer (740) or other control system is operatively connected to a control console (744), the control console (744) allows for manipulation of the computer (740) or other control system.

15. The method of claim 11, wherein the afterloading system (700) measures dwell time of the RBS (400) in the treatment position (118).

16. The method of claim 11, wherein the RBS (400) provides a dose rate of between about 1 to 10 Gy/min to the target.

17. The method of claim 11, wherein the cannula (100) comprises a distal portion (110) and a proximal portion (120) connected by an inflection point (130), the distal portion (110) has a radius of curvature between about 9 to 15 mm and an arc length between about 25 to 35 mm and the proximal portion (120) has a radius of curvature between about an inner cross-sectional radius of the cannula (100) and about 1 meter.

18. A method of irradiating a target of an eye in a patient, said method comprising:

(a) inserting a cannula (100) into a potential space between a sclera and a Tenon's capsule of the eye of the patient, the cannula (100) is operatively connected to an afterloading system (700) having a radionuclide brachytherapy source (RBS) (400);

(b) positioning the RBS (400) over the target;

(c) irradiating the target with the RBS (400); and (d) removing the cannula (100).

19. The method of claim 18, wherein the afterloading system (700) comprises:

(a) a vault (710) for storage of the RBS (400), wherein the RBS (400) is attached to an advancing means (722);

(b) a guide tube (720) extending from the vault (710), the guide tube (720) is removably attachable to the cannula (100); and (c) a source-drive mechanism (730) operatively connected to the advancing means (722), wherein the source-drive mechanism (730) advances the RBS (400) through the guide tube (720) to a treatment position (118) in the cannula (100).

20. The method of claim 19, wherein the source-drive mechanism (730) is operatively connected to a computer (740) or other control system.

* * * * *